United States Patent [19]

Tickner

[11] 4,316,391
[45] Feb. 23, 1982

[54] FLOW RATE MEASUREMENT
[75] Inventor: Ernest G. Tickner, Gilroy, Calif.
[73] Assignee: Ultra Med, Inc., Sunnyvale, Calif.
[21] Appl. No.: 93,525
[22] Filed: Nov. 13, 1979
[51] Int. Cl.³ .............................................. G01F 1/00
[52] U.S. Cl. .................................. 73/861.25; 128/663
[58] Field of Search ..................... 128/662, 663; 73/19, 73/23, 861.06, 25–26, 861.41

[56] References Cited

U.S. PATENT DOCUMENTS

| 3,640,271 | 2/1972 | Horton | 128/662 |
| 3,921,622 | 11/1975 | Cole | 128/663 |
| 4,122,713 | 10/1978 | Stasz et al. | 128/663 |

OTHER PUBLICATIONS

Tickner, E. G. et al., "Non-Invasive Assessment of Pulmonary Hypertension Using the Bubble UTS Resonance Pressure (BURP) Method", NHLB Tech. Rept. HR-62917-1A, Apr. 1977.
Feigenbaum, H., "Echocardiography", Chapter 2, pp. 5-54, 2nd Edition, Lea & Febiger Publ., Phila., Pa.

Primary Examiner—Robert W. Michell
Assistant Examiner—Francis J. Jaworski
Attorney, Agent, or Firm—Phillips, Moore, Weissenberger, Lempio & Majestic

[57] ABSTRACT

A method is presented for measuring fluid flow rate in a system having a conduit through which the fluid flows. The method is particularly useful for measuring blood flow rate in a cardiovascular system. A substance which provides a plurality of microbubbles is added to the fluid flow system upstream of the measurement position in the conduit. An ultrasonic pulse is generated from a position opposite and spaced from the conduit as the microbubbles pass therethrough. A reflected ultrasonic image, created by reflection of the pulse from at least the wall of the conduit which is distal from said position, is measured. The fluid flow rate within the conduit is determined from these ultrasonic images using dye dilution techniques. In a living being, the pulse is preferably generated adjacent the rib cage or in the esophagus and the conduit is preferably the heart or the pulmonary artery, whereby, the blood flow rate determined is equal to the volumetric cardiac output rate.

9 Claims, 5 Drawing Figures

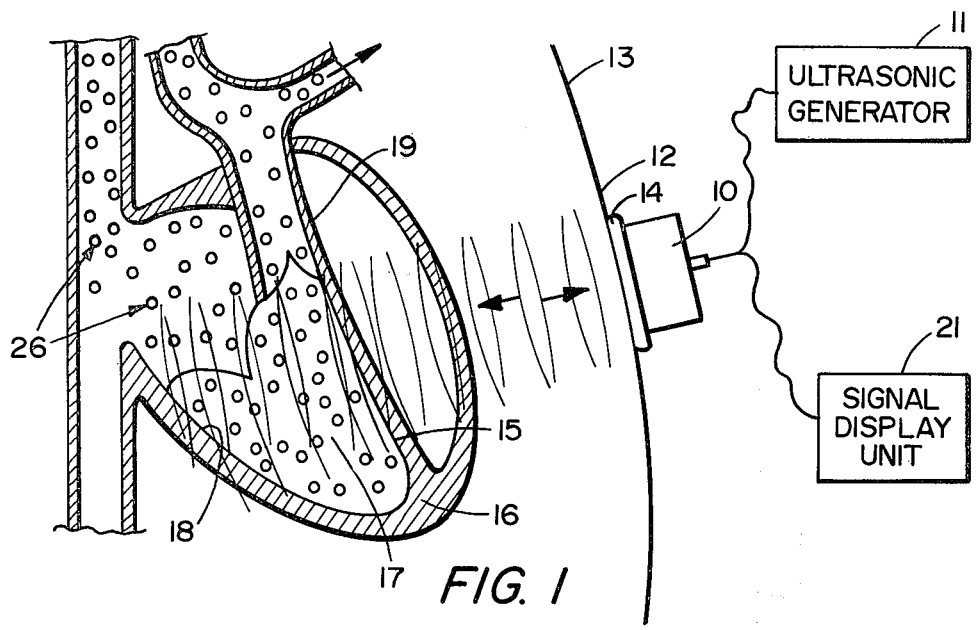
FIG. 1
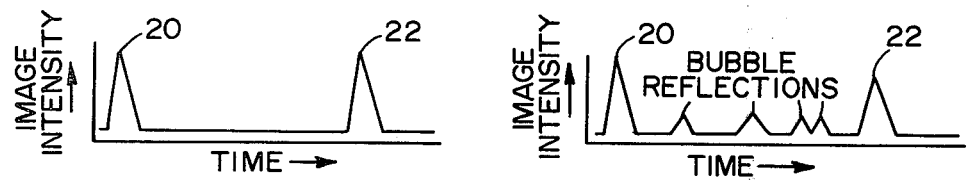
FIG. 2A
FIG. 2B
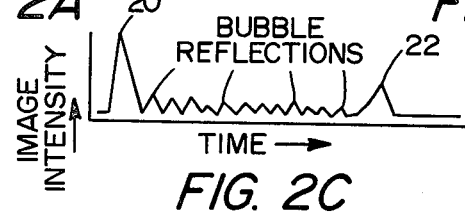
FIG. 2C
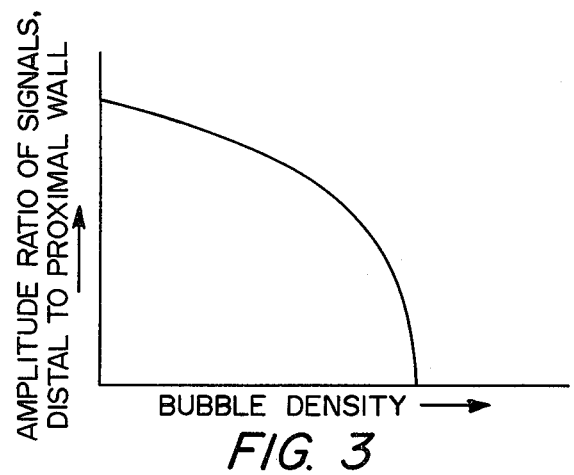
FIG. 3

FLOW RATE MEASUREMENT

BACKGROUND OF THE INVENTION

1. Field of the Invention

The invention relates to a method of measuring fluid flow rate in a system in which fluid flows via a conduit from one location therein to another. In particular, the method is advantageously used in measuring flow rate within the cardiovascular system of a living being.

2. Prior Art

One of the key cardiovascular parameters used by the cardiologist to diagnose and follow the progress of acutely ill cardiac patients is their cardiac output. Key to their treatment is the knowledge of this parameter. Cardiac output is generally measured using some form of dye dilution technique. For example, the "Fick" method measures the breathing rate and determines oxygen uptake as well as both venous and arterial blood oxygen level. The cardiac output can then be computed based on the sample values.

A number of flow rate measuring methods operate on the indicator-dilution-principle. For example, cold blood or a dye, may be injected, via a catheter inserted from downstream of the heart, backwardly therethrough and into the superior vena cava, from whence it will flow through the right atrium and right ventricle to the main pulmonary artery. In the case of cold blood, a pair of thermistors, or other temperature sensing instruments, are attached to the catheter, one slightly downstream of the point of injection and the other further downstream, generally corresponding to somewhere in the main pulmonary artery. A temperature versus time measurement at the first thermistor shows a sharp pulse, whereas, a temperature versus time measurement at the second thermistor shows a diffuse or spread out pulse. Through integration of the pulses, a measurement of blood flow through the heart (cardiac output) is thereby obtained. Similarly, the flow of a dye can be observed, e.g., using fiber optics, and correlated to cardiac output. A description of the theory behind the indicator-dilution method appears in the Handbook of Physiology-Circulation, Volume I, Chapter 18 at pages 585–591, American Physiologic Society, Washington D.C., 1962 and in Dye Curves D. A. Bloomfield, University Park Press, Baltimore, 1974.

The indicator-dilution methods of the prior art have required inserting catheters upstream through the heart with thermistors or dye flow detectors attached thereto, thus causing patient discomfort and, possibly traumatic shock. A finite risk is associated with routine usage of this procedure. In some patients such insertion is impossible because of the particular nature of the patient's heart valves which may not be known ahead of time. Further, the prior are methods have been subject to possible error due to somewhat uncertain positionings of the catheters and observations of the dye flow.

It would be advantageous to have an indicator-dilution method which did not suffer from the aforementioned problems. In particular, it would be advantageous to provide an indicator-dilution method wherein catheter insertion starting downstream of the heart and continuing therethrough was not necessary, and where the only invasion of the body itself was via injection of the indicator well upstream of the heart, for example, into the median cubital vein adjacent the elbow. It would also be advantageous if accurate measurement techniques for the flow of the indicator were to form a part of such a method, whereby possible operator error was eliminated or at least minimized.

SUMMARY OF THE INVENTION

The invention relates to a method of measuring fluid flow rate in a system having a conduit through which a fluid flows. The method comprises adding a substance which provides a plurality of bubbles of a known quantity and size to the system upstream of the conduit. A sonic pulse is generated from a position opposite and spaced from the conduit as the bubbles pass therethrough. Reflected sonic images are measured, which images are created by reflection of the pulse from the wall of the conduit distal from the position. Additionally, other reflections are measured from the bubbles themselves flowing between the two walls. The fluid flow rate is then determined from the sonic images.

BRIEF DESCRIPTION OF THE DRAWINGS

The invention will be better understood by reference to the figures of the drawings, wherein like numbers denote like parts throughout, and wherein:

FIG. 1 illustrates, schematically, a method in accordance with the present invention in practice with a living being;

FIGS. 2A, 2B and 2C illustrate, graphically, reflected sonic images as a function of bubble density as measured in accordance with the method of the present invention; and FIG. 3 illustrates, graphically, an empirical relationship which has been found between the amplitude ratio of the distal wall to proximal wall reflected sonic image signals as a function of bubble density.

DETAILED DESCRIPTION OF THE PREFERRED EMBODIMENT

The introduction of bubbles, particularly microbubbles, into a flowing system such as the cardiovascular system of a living test subject is known and is discussed in copending applications Ser. Nos. 36,098, filed May 4, 1979, of E. G. Tickner and N. Rasor and 52,745, filed June 28, 1979 of E. G. Tickner. The disclosures of both of these applications are hereby incorporated herein by reference thereto.

The term "bubble" is used herein to denote bubbles of any size and the term "sonic" is used herein to denote sound of any frequency. The term "microbubbles" is used herein to denote bubbles which efficiently reflect ultrasonic signals, generally bubbles of no more than about 325 microns in diameter.

The production of freely flowing microbubbles of a controlled size and their injection into the bloodstream for different diagnostic techniques is known. The present inventor, along with N. Rasor, in a report entitled "Non-Invasive Assessment of Pulmonary Hypertension Using The Bubble Ultrasonic Resonance Pressure (BURP) Method" (Report NO1-HR-62917-1A), April, 1977 sponsored by the Division of Lung Diseases, National Heart, Lung and Blood Institute, report on the production and the attempt to use such bubbles for non-invasively measuring pulmonary artery blood pressure by sensing bubble ultrasonic resonance. Basically, microbubbles are injected into a peripheral vein and their ultrasonic resonance re-emission frequency is measured as they pass through the pulmonary artery. The re-emission resonance frequency (about 100 kHz or less) is determined by sweeping the excitation frequency about bubble resonance and by applying an ultrasonic receiver probe to the chest of the subject to detect bubble resonance which gives the maximum backscattering signal.

Either membrane surrounded microbubbles or shell encapsulated microbubbles may be used in practicing the present invention. Both types of microbubbles are discussed below.

Membrane Surrounded Microbubbles

The microbubble producing substance may be a plurality of microbubbles, each having a surface membrane which encapsulates a gas of a selected composition. The structure of the membrane is of extreme importance. It should be selected to reduce coalescence and must include a multiplicity of non-toxic and non-antigenic organic molecules. Gelatin is particularly preferred as the membrane material.

The organic molecules which form a gelatin membrane are believed to have both a hydrophilic portion and a hydrophobic portion. When the membrane-covered microbubbles are in the bloodstream, the hydrophilic portions are believed to be aligned radially outwardly or away from the centers of the respective microbubbles. As a result, the microbubbles tend to repel one another, thus significantly reducing the tendency of the microbubbles to coalesce with one another and form larger microbubbles.

Membranes other than gelatin and having resistance to coalescing, as well as non-toxic and non-antigenic properties, are also suitable whether the resistance to coalescing is due to the presence of such hydrophilic and hydrophobic portions, to particularly strong membranes, or whatever. This resistance to coalescing is important in ensuring that the sizes of the microbubbles in the bloodstream are substantially the same for microbubbles which are originally of the same size and have been in the bloodstream an equal length of time. With time, of course, the gas or gases contained within the membranes will dissolve into the bloodstream and the microbubbles will be gradually reduced in size until they disappear.

For use within the bloodstream it is essential that the organic molecules which form the membrane be non-toxic and non-antigenic, since it is clear that either a toxic or antigenic reaction within the bloodstream is highly undesirable.

With respect to the gas within the membrane, a chemically inert and somewhat slowly dissolving gas such as nitrogen or one of the slower dissolving noble gases is very suitable. In other instances, it may be desirable to employ a gas which dissolves in blood quickly, such as carbon dioxide.

The size of such bubbles as are used in the bloodstream is also important. Generally they will be microbubbles, at most, about 325 microns, and at least about 0.5 micron, in diameter. The frequency of the ultrasonic pulse will generally be chosen to obtain good reflection from the particular size microbubbles in the blood. More preferably, the microbubbles will have a diameter below about 150 microns and above about 1.0 micron.

Such microbubbles as have just been described can be produced by gradually flowing a gas through a small orifice, for example through a capillary tube, and into a liquid. A force is generally exerted upon the microbubble being formed at the orifice, with the force being sufficient to remove the microbubble prior to its attaining the full size it would attain in the absence of such force. For example, the orifice may lie generally in a vertical plane (the capillary may be horizontal) and the force may simply comprise the buoyancy of the microbubble in the liquid and the surface tension attachment to the orifice. Alternatively, and preferably, the orifice may lie in any orientation with respect to flow past the orifice, and the force consists of fluid drag on the bubble and the surface tension force. In both situations, the microbubbles may flow into a storage container such as a hypodermic syringe. The aforementioned report "Non-Invasive Assessment of Pulmonary Hypertension Using The Bubble Ultrasonic Resonance Pressure (BURP) Method" describes production of such microbubbles in more detail.

Other methods of producing the described microbubbles have been successfully employed. For example, microbubbles have been created by supersaturation of a liquid; air or liquid jet impingement upon a free liquid surface; and addition of $NaHCO_3$ particles to a liquid. These latter methods permit production of large quantities of microbubbles but of a much broader spectrum of sizes than the highly uniform diameter of microbubbles produced by a submerged orifice.

It is preferred that the microbubbles be formed and dispersed in a medium having a chemical composition substantially identical to that of the membrane. It is further preferred that the medium be gellable. As previously mentioned, a particularly preferred membrane material is gelatin itself, because it is well-known to be non-toxic, non-antigenic and non-allergenic. Utilizing a gellable medium allows the microbubble dispersion to be stored for extended periods of time by simply lowering the temperature of the medium sufficiently so that gelling occurs. In practice, the gelled microbubble dispersion is stored in hypodermic syringes. When needed, the gelatin is melted by warming the syringes, and the dispersion is injected into a blood vessel. The bulk of the gelatin dissolves in the blood, leaving the required gelatin stabilizing membrane around each microbubble.

Shell Encapsulated Microbubbles

A solid bubble precursor may alternatively be added to the blood which fills the cardiovascular system. The precursor particles are carried along with the blood flow in the manner just described. Generally the particles would be injected into the bloodstream upstream of the heart and then would be carried therethrough by the blood flow.

The particles serve as microbubble precursors in a method which will be explained. Briefly, the solid microbubble precursors or particles will generally comprise a hollow interior space completely enclosed by an outer surrounding shell or wall. The outer surrounding wall will generally be of a saccharide composition. A particular preferred composition is approximately 80% sucrose and 20% lactose. The hollow space will generally be filled with a gas, generally at a pressure of 1 atmosphere or above. Such compositions as have just been described for the particles can be formed generally as described in U.S. Pat. No. 3,012,873, issued Dec. 12, 1961 to L. Kremzner and W. A. Mitchell, The amount of gas in the hollow space of each one of the particles will be generally about the same so that when the outer wall of each particle dissolves sufficiently to allow the gas to escape from the hollow space, the resulting microbubbles formed in the cardiovascular system will be of a uniform size.

It has been found that if a viscous sugar solution, of the composition set out in U.S. Pat. No. 3,012,873, is flowed through a tube, with the temperature of the sugar solution being held just a few degrees above the solidification point thereof, and if an end of the tube exists into a cooled zone which is at a temperature below the solidification temperature of the viscous sugar liquid, and if a gas such as carbon dioxide is introduced generally centrally into the flowing liquid via a capillary tube, with an end of the capillary tube being at or near an end of the sugar flow tube, then as the sugar quickly solidifies, the amount of carbon dioxide or other gas trapped in each of the resulting quickly solidified microbubble precursor particles, is substantially equal. The apparatus may be kept at any desired pressure, for example, 1 to 50 atmospheres. A liquid jet is created containing the microbubbles. The flow jet is made unstable to create dynamic (Rayleigh) instability, whereby particles are produced having as few as possible hollow spaces per particle. Preferably, one hollow space per particle with uniform wall thickness is ideal, although particles with thirty or more hollow spaces each work quite adequately in the method of the present invention.

Generally, the amount of gas entrapped within each one of the particles is controlled so that when a microbubble is produced therefrom, it will be generally within a range from about 325 microns to about 0.5 microns in diameter. More preferably, the microbubbles would have a diameter below about 150 microns and above about 1.0 micron, as with the membrane surrounded microbubbles previously discussed.

Use In The Indicator-Dilution Method

It has been discovered that such bubbles, particularly such microbubbles as are described in the previously mentioned two pending U.S. Patent Applications, can be utilized as part of a novel indicator-dilution method for determining blood flow rate and blood volume, or for that matter flow rate and volume of other flowing systems. In accordance with the invention, and as will be particularly clear by reference to FIG. 1, an exciter (transducer) 10 powered by an ultrasonic generator 11 may be placed against the chest 12 of a living test subject 13, generally adjacent the rib cage. Alternatively, the transducer 10 may be positioned via an esophageal probe. A small amount of acoustical coupling gel 14 is placed between the transducer and the skin to improve acoustic transmission. An ultrasonic signal is generated by the transducer 10 and a reflected ultrasonic image is measured by the same transducer 10. It is common practice to use the same transducer as both an exciter and a receiver. When this is done, the transducer functions as a receiver about 99.9% of the time. Alternatively, a separate adjacent receiver may be utilized. A reflected signal is received from a proximal wall 15 of the heart 16, generally from adjacent the right ventricle 17 (although the left ventricle can also be used as the measurement vessel). A second reflected signal is received at a later time from a distal wall 18 of the heart 16. The blood with the microbubbles is discharged from the right ventricle into the pulmonary artery 19. The transducer 10 can be placed opposite the main pulmonary artery 19, if desired, and measurements may be taken from that vessel rather than from the right ventricle. In either case, the volumetric cardiac output may be determined.

The representation in FIG. 2A shows the signal that is received in the absence of any microbubbles in the heart 16. A peak 20, as produced by a signal display unit 21, e.g., an oscilloscope or recorder, represents the reflected signal from the proximal wall 15. A peak 22 represents the reflected signal from the distal wall 18.

In accordance with the invention, a substance of known microbubble quantity and size is inserted upstream of the heart, for example, upstream of the superior vena cava 24, as at the median cubital vein. This provides a plurality of microbubbles 26 within the heart 16. The microbubbles 26 within the heart 16 serve to scatter a portion of the ultrasonic pulse generated by the exciter 10. Thus, the amount of energy being reflected at the distal wall 18 is attenuated and signals are obtained which bounce back from the bubbles 26.

The representations in FIGS. 2B and 2C show the effect of having microbubbles 26 in the heart 16, with FIG. 2B representing a lower concentration of microbubbles 26 than does FIG. 2C. It is clear from examination of FIGS. 2A, 2B and 2C that a ratio, of the intensity (amplitude) of the peak 22 to the peak 20, decreases with more bubbles in the heart 16.

FIG. 3 shows the empirical relationship which has been found between microbubble density within the pulmonary artery 19 and the amplitude ratio of the peak 22 from the distal wall 18 to the peak 20 from the proximal wall 15. A unique functional relationship exists which can be used to determine bubble density.

From information measured as just described above, and particularly from the reflected ultrasonic image, the bubble concentration can be determined, and then the fluid flow rate, in the particular embodiment illustrated the cardiac output, can be determined from the known equation set out in The Handbook of Physiology-Circulation and in Dye Curves.

It is also possible to simply determine the ratio of the reflected signal (peak 22) with a known quantity of microbubbles of a known size to the reflected signal (peak 22) of blood alone. The same equations can then be used to determine cardiac output. This is somewhat less accurate as it ignores the relatively small reflectivity of the blood.

When operating as just described, it is clear that it is not necessary to pass a catheter upstream into the heart. This eliminates the problem of potential valve damage and allows measurements in those individuals wherein such catherization cannot be reasonably readily accomplished. It also makes available cardiac output measurements as a standard clinical procedure because it is considered medically noninvasive. Patient discomfort is greatly reduced and the possibility of shock and sudden death is virtually eliminated. The only invasion of the body is generally by a hypodermic syringe inserted, generally, at the median cubital vein, whereat either a bolus of microbubble providing substance is injected or a steady flow of microbubble providing substance is injected.

While the invention is described in detail with respect to measurement of blood flow rate, and particularly cardiac output, it should be clear that it is also useful in other systems wherein fluid is flowing. In such systems the signals generated and reflected need not be ultrasonic and the bubbles need not be microbubbles.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method of measuring fluid flow rate in a system having a conduit through which fluid flows, comprising:

adding a substance which provides a plurality of bubbles of known size to said system upstream of said conduit;

impelling a sonic pulse across said conduit, from a position opposite and spaced from said conduit, as said bubbles pass therethrough;

measuring the degree of attenuation of a sonic signal defined by said pulse which passes across said conduit, said attenuation being due to the presence of said bubbles; and determining the fluid flow rate from the degree of attenuation of said sonic signal.

2. A method as in claim 1, wherein said measuring step includes measuring a reflected sonic signal created by reflection of said pulse from a wall of said conduit proximal to said position.

3. A method as in claim 2, wherein said determining step includes determining a ratio of the intensities of those portions of the signal reflected from the proximal and distal walls, and determining bubble density in said conduit from said ratio.

4. A method as in claim 1, wherein said system is a cardiovascular system of a living being, said bubbles are microbubbles, said sonic signal is an ultrasonic signal and said fluid is blood.

5. A method as in claim 4, wherein said position whereat said pulse is generated is a respective one of adjacent a rib cage and within an esophagus of said living being, said conduit is a respective one of a heart and a pulmonary artery, and said blood flow rate is the volumetric cardiac output rate.

6. A method as in claim 4, wherein said measuring step includes measuring a reflected sonic signal created by reflection of said pulse from a wall of said conduit proximal to said position and wherein said determining step includes determining a ratio of the intensities of those portions of the signal reflected from the proximal and distal walls and determining microbubble density in said conduit from said ratio.

7. A method as in claim 1, wherein said adding is of a bolus of said bubbles.

8. A method as in claim 1, wherein said adding is during a selected time period.

9. A method as in claim 1, wherein said degree of attenuation measured is that of a selected portion only of said sonic signal.

* * * * *